United States Patent
Thennati et al.

(10) Patent No.: US 10,138,221 B2
(45) Date of Patent: Nov. 27, 2018

(54) SALTS OF NILOTINIB AND POLYMORPHS THEREOF

(71) Applicant: Sun Pharmaceutical Industries Limited, Mumbai (IN)

(72) Inventors: Rajamannar Thennati, Mumbai (IN); Srinivasu Kilaru, Mumbai (IN); Macwan Valance Surendrakumar, Mumbai (IN); Dwivedi Shriprakash Dhar, Mumbai (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 0 days.

(21) Appl. No.: 15/503,144

(22) PCT Filed: Aug. 10, 2015

(86) PCT No.: PCT/IN2015/050086
§ 371 (c)(1),
(2) Date: Feb. 10, 2017

(87) PCT Pub. No.: WO2016/024289
PCT Pub. Date: Feb. 18, 2016

(65) Prior Publication Data
US 2017/0233372 A1    Aug. 17, 2017

(30) Foreign Application Priority Data
Aug. 11, 2014    (IN) .......................... 2583/MUM/2014

(51) Int. Cl.
*C07D 401/14*    (2006.01)
(52) U.S. Cl.
CPC ........ *C07D 401/14* (2013.01); *C07B 2200/13* (2013.01)

(58) Field of Classification Search
CPC .................................................. C07D 401/14
See application file for complete search history.

(56) References Cited

U.S. PATENT DOCUMENTS 6,479,692 B1 * 11/2002 Ekwuribe ............. C07C 253/30
558/413
8,703,788 B2 * 4/2014 Reddy .................. A61K 31/506
514/275

FOREIGN PATENT DOCUMENTS

| CN | 103864756 | * | 6/2014 |
| CN | 104644543 | * | 5/2015 |
| WO | 2007/015871 A1 | | 2/2007 |
| WO | 2008/037716 A2 | | 4/2008 |

OTHER PUBLICATIONS

Berge et al., "Pharmaceutical Salts";m Journal of Pharmaceutical Sciences, vol. 66, No. 1, pp. 1-19; Jan. 1977.*
CAS Abstract CN 104644543 (2015).*
CAS Abstract CN 103864756 (2015).*
Written Opinion of the International Searching Authority of PCT/IN2015/050086 dated Jul. 15, 2016.
International Search Report of PCT/IN2015/050086 dated Jul. 15, 2016.

* cited by examiner

*Primary Examiner* — Alexander R Pagano
*Assistant Examiner* — Ebenezer O Sackey
(74) *Attorney, Agent, or Firm* — Sughrue Mion, PLLC (57) ABSTRACT

The present invention provides novel salts of nilotinib and polymorphs thereof. The acid addition salts of nilotinib with benzenesulfonic acid, butanedisulfonic acid, 1-5-naphthalenedisulfonic acid, naphthalene-1-sulfonic acid and 1-hydroxynaph-thoic acid; hydrates and anhydrates thereof.

25 Claims, 8 Drawing Sheets

Fig 1: XRD of Form I Nilotinib benzenesulfonate of Example 1.

Fig 2: XRD of Form II nilotinib butanedisulfonate (2:1) of Example 2.

Fig 3: XRD of Form III nilotinib butanedisulfonate (2:1) of Example 4.

Fig 4: XRD of From IV nilotinib butanedisulfonate (1:1) of Example 6.

Fig 5: XRD of Form V nilotinib 1-5-naphthalenedisulfonate (2:1) of Example 7.

Fig 6: XRD of nilotinib 1-5-naphthalenedisulfonate (1:1) of Example 8.

Fig 7: XRD of nilotinib naphthalene-1-sulfonate of Example 9.

Fig 8: XRD of nilotinib 1-hydroxynaphthoate of Example 10.

SALTS OF NILOTINIB AND POLYMORPHS THEREOF

CROSS REFERENCE TO RELATED APPLICATIONS

This application is a National Stage of International Application No. PCT/IN2015/050086 filed Aug. 10, 2015, claiming priority based on Indian Patent Application No. 2583/MUM/2014 filed Aug. 11, 2014, the contents of all of which are incorporated herein by reference in their entirety.

FIELD OF INVENTION

The present invention relates to novel salts of nilotinib and polymorphs thereof. Particularly, the present invention provides acid addition salts of nilotinib with butanedisulfonic acid, 1-5-naphthalenedisulfonic acid, benzenesulfonic acid, naphthalene-1-sulfonic acid and 1-hydroxynaphthoic acid and hydrates, anhydrates thereof.

BACKGROUND OF THE INVENTION

Nilotinib, 4-methyl-N-[3-(4-methyl-1H-imidazol-1-yl)-5-(trifluoromethyl)phenyl]-3-[[4-(3-pyridinyl)-2-pyrimidinyl]amino]-benzamide, having the following formula is marketed under the name Tasigna® in US and Europe. Tasigna contains nilotinib monohydrate monohydrochloride salt and is available as capsules for the treatment of adult patients with newly diagnosed Philadelphia chromosome positive chronic myeloid leukemia (Ph+ CML) in chronic phase. Tasigna is also indicated for the treatment of chronic phase and accelerated phase Philadelphia chromosome positive chronic myelogenous leukemia (Ph+ CML) in adult patients resistant or intolerant to prior therapy that included imatinib.

Nilotinib is considered a low solubility/low permeability (class IV) compound in the Biopharmaceutics Classification System (BCS). Therefore, dissolution of nilotinib can potentially be rate limiting step for in-vivo absorption. It is soluble in acidic media; being practically insoluble in buffer solutions of pH 4.5 and higher.

WIPO publication 2014059518A1 discloses crystalline forms of nilotinib hydrochloride and methods of the preparation of various crystalline solvates of nilotinib hydrochloride including benzyl alcohol, acetic acid and propylene glycol.

WIPO publication 2011033307A1 discloses nilotinib dihydrochloride and its hydrates and method for their preparation.

WIPO publication 2011163222A1 discloses the preparation of nilotinib salts and crystalline forms thereof. The salts of nilotinib disclosed are hydrochloride, fumarate, 2-chloromandelate, succinate, adipate, L-tartrate, glutarate, p-toluenesulfonate, camphorsulfonate, glutamate, palmitate, quinate, citrate, maleate, acetate, L-malate, L-aspartate, formate, hydrobromide, oxalate and malonate.

WIPO publication number 2011086541A1 discloses a nilotinib monohydrochloride monohydrate salt and methods for preparing.

WIPO publication number 2010054056A2 describes several crystalline forms of nilotinib hydrochloride.

WIPO publication number 2007/015871A1 discloses the preparation of nilotinib salts and crystalline forms thereof. The salts are mixtures of nilotinib and one acid wherein the acids are selected from the group consisting of hydrochloric acid, phosphoric acid, sulfuric acid, sulfonic acid, methane sulfonic acid, ethane sulfonic acid, benzene sulfonic acid, p-toluene sul-fonic acid, citric acid, fumaric acid, gentisic acid, malonic acid, maleic acid, and tartaric acid.

WIPO publication number 2007015870A2 discloses several nilotinib salts including amorphous and crystalline forms of nilotinib free base, nilotinib HCl and nilotinib sulfate along with their hydrate and solvates.

SUMMARY OF INVENTION

The present inventors have found novel salts of nilotinib and polymorphs thereof, with advantageous properties.

More specifically, the present invention provides acid addition salt of nilotinib wherein the acid is selected from benzenesulfonic acid, butanedisulfonic acid, 1-5-naphthalenedisulfonic acid, naphthalene-1-sulfonic acid and 1-hydroxynaphthoic acid and hydrates, anhydrates thereof, have been found to posses advantageous properties.

The salts of present invention provide improved dissolution and solubility profile. Further the salts of the present invention can be crystallized into polymorphs which provide advantages in improved flow property, ease of handling and processing.

DETAILED DESCRIPTION OF THE INVENTION

The present invention provides novel salts of nilotinib.

In one aspect, present invention provides acid addition salt of nilotinib wherein the acid is selected from benzenesulfonic acid, butanedisulfonic acid, 1-5-naphthalenedisulfonic acid, naphthalene-1-sulfonic acid and 1-hydroxynaphthoic acid and hydrates, anhydrates thereof.

The acid addition salts of the present invention can be prepared by reacting a solution of nilotinib base in a suitable solvent with the respective acid. The reaction may be carried out at elevated temperature to falicitate the reaction. The salts may be isolated form the reaction mixture by any of the general techniques known in the art.

In one embodiment, the present invention provides acid addition salt of nilotinib wherein the acid is benzenesulfonic acid. In another embodiment, the present invention provides a crystalline Form I of nilotinib benzenesulfonate having an X-ray powder diffraction pattern comprising characteristic peaks at 7.2, 14.5, 18.8 and 24.2±0.2 degrees 2θ. In another embodiment the Form I has X-ray powder diffraction pattern comprising further characteristic peaks at 20.7, 25.7, 26.2 and 29.1±0.2 degrees 2θ.

In one embodiment, the present invention provides acid addition salt of nilotinib wherein the acid is butanedisulfonic acid. In another embodiment the salt of nilotinib with butanedisulfonic acid has mole ratio of nilotinib to butanedisulfonic acid as 2:1. In another embodiment the present invention provides a crystalline Form II of 2:1 salt of nilotinib with butanedisulfonic acid having water content of 3% to 10%. In another embodiment the crystalline Form II is a hydrate. In another embodiment the crystalline Form II has an X-ray powder diffraction pattern comprising characteristic peaks at 5.9, 8.1, 26.3 and 26.9±0.2 degrees 2θ. In another embodiment the crystalline Form II comprises further characteristic peaks at 19.6, 21.1, 21.9 and 27.5±0.2 degrees 2θ in its X-ray powder diffraction pattern.

In another embodiment the present invention provides a crystalline Form III of 2:1 salt of nilotinib with butanedisulfonic acid having water content of less than 1%. In another embodiment the crystalline Form III has an X-ray powder diffraction pattern comprising characteristic peaks at 10.0, 20.3, 20.9 and 25.2±0.2 degrees 2θ. The crystalline Form III comprises further characteristic peaks at 5.8, 14.9, 17.3 and 25.9±0.2 degrees 2θ in its X-ray powder diffraction pattern.

In another embodiment the salt of nilotinib with butanedisulfonic acid has mole ratio of nilotinib to butanedisulfonic acid as 1:1. In another embodiment present invention provides a crystalline Form IV of 1:1 salt of nilotinib with butanedisulfonic acid having an X-ray powder diffraction pattern comprising characteristic peaks at 6.7, 20.2, 20.7, 24.3, and 25.7±0.2 degrees 2θ. In another embodiment the crystalline Form IV comprises further characteristic peaks at 14.8, 16.6, 17.9 and 28.2 degrees 2θ in its X-ray powder diffraction pattern.

In another embodiment the present invention provides the acid addition salt of nilotinib wherein the acid is 1,5-naphthalene sulfonic acid. In another embodiment the the mole ratio of nilotinib to 1,5-naphthalene sulfonic acid acid is 2:1. In another embodiment the present invention provides a crystalline Form V of 2:1 salt of nilotinib with 1,5-naphthalene sulfonic acid having an X-ray powder diffraction pattern comprising characteristic peaks at 15.3, 17.5, 21.3 and 26.2±0.2 degrees 2θ. The crystalline Form V comprises further characteristic peaks at 7.5, 10.2, 18.8 and 19.3±0.2 degrees 2θ in its X-ray powder diffraction pattern.

In another embodiment the present invention provides a salt of nilotinib with 1,5-naphthalene sulfonic acid wherein the mole ratio of nilotinib to 1,5-naphthalene sulfonic acid is 1:1. In another embodiment the present invention provides a crystalline Form VI of 1:1 salt of nilotinib with 1,5-naphthalene sulfonic acid having an X-ray powder diffraction pattern comprising characteristic peaks at 18.8, 19.5, 25.4 and 26.1±0.2 degrees 2θ. In another embodiment the crystalline Form VI comprises further characteristic peaks at 5.0, 9.9, 16.3 and 24.6±0.2 degrees 2θ in its X-ray powder diffraction pattern.

In another embodiment the present invention provides naphthalene-1-sulfonate salt of nilotinib. In another embodiment present invention provides a crystalline Form VII of nilotinib naphthalene-1-sulfonate having an X-ray powder diffraction pattern comprising characteristic peaks at 21.4, 24.5, 26.2 and 27.1±0.2 degrees 2θ. In another embodiment the crystalline Form VII comprises further characteristic peaks at 12.8 and 15.3±0.2 degrees 2θ in its X-ray powder diffraction pattern.

In another embodiment the present invention provides the acid addition salt of nilotinib wherein the acid is 1-hydroxynaphthoic acid. In another embodiment present invention provides a crystalline Form VIII of a salt of nilotinib with 1-hydroxynaphthoic acid having an X-ray powder diffraction pattern comprising characteristic peaks at 7.2, 24.9, 25.8 and 26.3±0.2 degrees 2θ. In another embodiment the crystalline Form VIII comprises further characteristic peaks at 9.2, 9.5, 13.1 and 13.9±0.2 degrees 2θ in its X-ray powder diffraction pattern.

The nilotinib salts and their crystalline forms of the present invention can be used for the treatment of disease which responds to an inhibition of protein kinase activity. In an embodiment the present invention provides acid addition salt of nilotinib or crystalline form thereof wherein the acid is selected from benzenesulfonic acid, butanedisulfonic acid, 1-5-naphthalenedisulfonic acid, naphthalene-1-sulfonic acid and 1-hydroxynaphthoic acid, for use in medicine.

In another embodiment the present invention provides acid addition, or crystalline form of, salt of nilotinib as per the present invention for use in in the treatment of leukemia. In a preferred embodiment the leukemia is chronic myeloid leukemia.

In another embodiment the present invention provides a method of treating a disease in a subject in need thereof comprising administering to the subject a therapeutically effective amount of an acid addition, or crystalline form of, salt of nilotinib of the present invention. In a preferred embodiment the disease is leukemia.

The present invention is further illustrated in detail with reference to the following examples. It is desired that the examples be considered in all respect as illustrative and are not intended to limit the scope of the claimed invention.

EXAMPLES:

Example 1

Preparation of Nilotinib Benzenesulfonate Crystalline Form I

Nilotinib base (1 g) was suspended in water (20 ml). A solution of benzenesulfonic acid (0.4 g) in water (3 ml) was added and the content was heated at 60° C. for 2-3 h. The mixture was cooled to 25-30° C., filtered, washed with water (3×5 ml) and dried under vacuum for 2 h at 50-55° C.

$^1$H NMR (500 MHz, DMSO-d6) δ 2.40 (s,3H), 2.42 (s,3H), 7.35-7.37 (m,3H), 7.51-7.66 (m,5H),7.83 (d,1H), 7.96 (s,1H),8.08 (s,1H),8.30 (s,1H) 8.39 (s,1H),8.54 (d,1H), 8.61 (d,1H), 8.64 (s,1H), 8.75 (d,1H), 9.25 (s,1H), 9.34 (d,1H), 9.61 (s,1H), 10.84 (s,1H).

Figure 1:
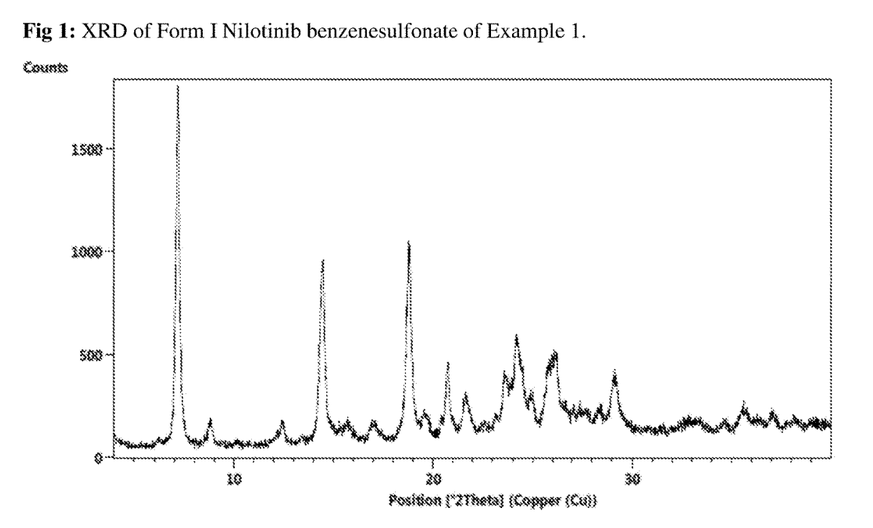
FIG. 1: XRD of Form I nilotinib benzenesulfonate of Example 1.

The salt provides an XRPD pattern substantially same as set forth in FIG. 1.

Example 2

Preparation of Nilotinib Butanedisulfonate (2:1) Crystalline Form II

Nilotinib base (100 g) was dissolved in 20% water in THF solution (2000 ml) at 60-65° C. and insoluble matter was filtered. The filtrate was concentrated under vacuum below 60° C. Filtered water (1000 ml) was added to the reaction mixture and it was heated at 50-55° C., followed by addition of 1,4-butanedisulfonic acid ~60% aqueous solution (28.6 ml) at same temperature. The content was stirred at 50-55° C. for 2-3h. Reaction mixture as cooled to 25-30° C. and product was filtered, washed with water (200 ml×2) and dried in air oven at 50-55° C. (yield: 115 g).

Purity (by HPLC):99.76%

$^1$H NMR (400 MHz,DMSO-d6) δ 1.63-1.66(m,2H), 2.40 (d,3H),2.42(s,3H),2.43-2.47(m,2H), 7.51-7.62(m,3H),7.85 (dd,1H),7.96(s,1H),8.08(s,1H),8.34(s,1H),8.38(d,1H),8.52-8.55(m,1H), 8.60-8.62 (m,2H), 8.75(d,1H), 9.25(s,1H),9.34 (s,1H),9.59(s,1H),10.86(s,1H)

Water content: 7.95%.

Figure 2:
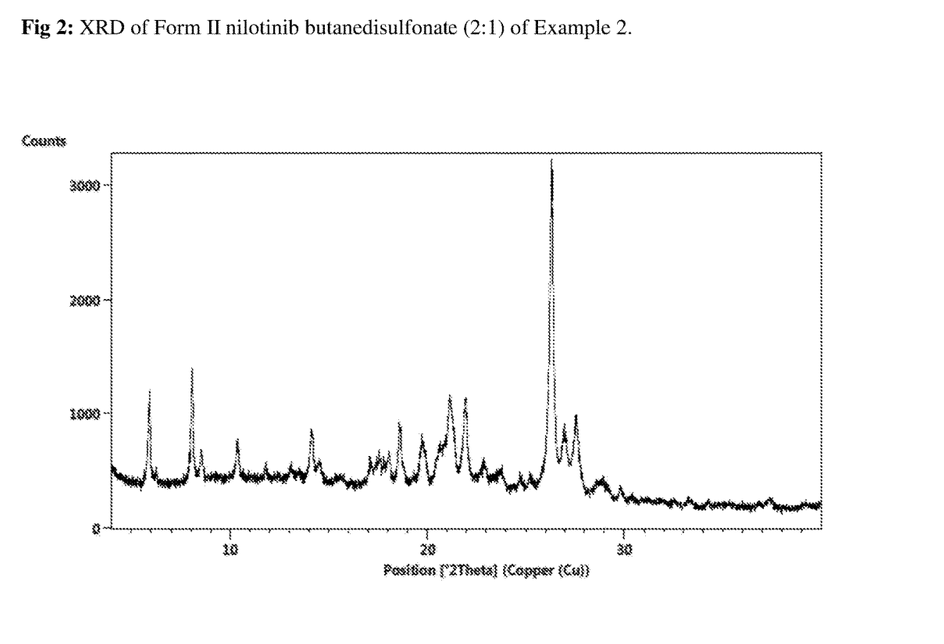
FIG. 2: XRD of Form II nilotinib butanedisulfonate (2:1) of Example 2.

The salt has a XRPD pattern substantially same as set forth in FIG. 2.

Example 3

Preparation of Nilotinib Butanedisulfonate (2:1) Crystalline Form II

Nilotinib base (300 g) was suspended in methanol (3000 ml) and aqueous hydrochloric acid was added to get pH less than 2. Reaction contents were heated at reflux and was filtered and washed with methanol (100 ml). 5% (w/w) NaOH (1200 ml) solution was added at 40-45° C. within 15 min, reaction mixture was stirred for 2h. Product was filtered, washed with water (300 ml×3) and dried for 1 h. Wet material was suspended in water (3000 ml), heated at 50-55° C. followed by addition of 1,4-butanedisulfonic acid ~60% aqueous solution. The reaction mixture was stirred at 50-55° C. for 2 hrs. Product was filtered at room temperature, washed with water (500 ml×2) and dried in air oven at 50-55° C. (yield: 293 g). Purity (by HPLC): 99.88%

$^1$H NMR (400 MHz,DMSO-d6+TFA-d1) δ 1.75-1.78(m, 2H), 2.36(d,3H),2.38(s,3H),2.69-2.72(m,2H),7.45(d,1H), 7.68(d,1H),7.83(s,1H),7.88(dd,1H),7.97(s,1H),8.16-8.19 (m,1H), 8.35 (s,2H), 8.63(d,1H),8.68(d,1H),9.04(d,1H),9.21 (d,1H),9.53(br s,1H),9.69(d,1H)10.80 (s,1H)

Water content: 6.44%

Example 4

Preparation of Nilotinib Butanedisulfonate (2:1) Crystalline Form III

Nilotinib butanedisulfonate (210g) was dissolved in acetic acid water mixture (50:50) (2520 ml) at 75-80° C. and was filtered to remove insoluble matter and washed with acetic acid water mixture (50:50) (210 ml). Water (3150 ml) was added to the filtrate and stirred first at room temperature and then at 0-5° C. Product was filtered and washed with water. Material was dried in air oven at 70-75° C. Dried material was leached with methanol (3438 ml) at reflux temperature, filtered and dried in air oven 70-75° C. (yield: 152.6 g)

Purity (by HPLC): 99.89%

$^1$H NMR (400 MHz,DMSO-d6+TFA-d1) δ 1.73-1.77(m, 2H), 2.40(s,6H),2.67-2.70(m,2H), 7.50 (d,1H), 7.70(d,1H), 7.88-7.92(m,2H), 8.07(s,1H),8.23 (dd,1H), 8.34(s,2H), 8.67 (d,1H), 8.72 (d,1H), 9.09(d,1H), 9.23 (s,1H), 9.54(d,1H), 9.74(d,1H), 10.86(s,1H).

Water content: 0.61%

Figure 3:
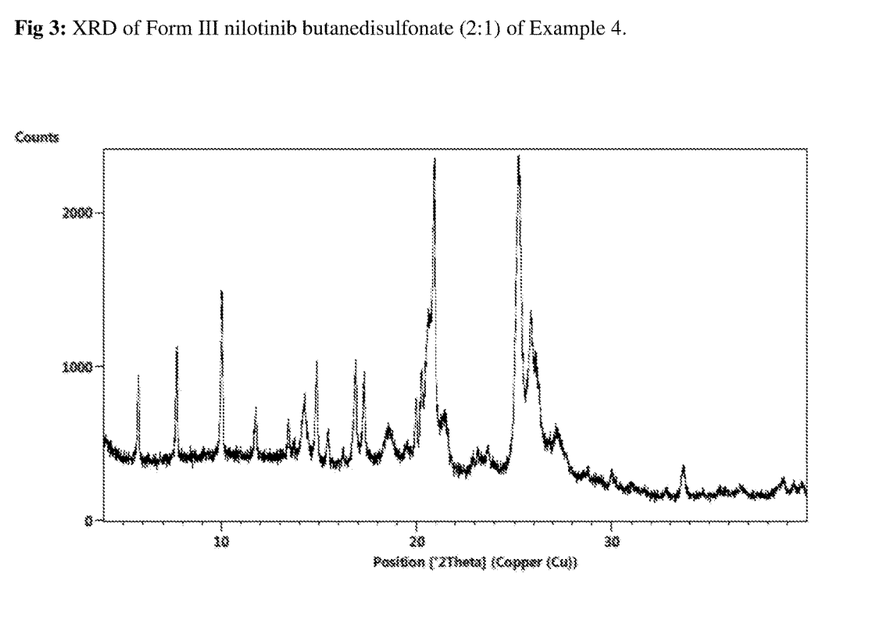
FIG. 3: XRD of Form III nilotinib butanedisulfonate (2:1) of Example 4.

The salt provides an XRPD pattern substantially same as set forth in FIG. 3.

Example 5

Preparation of Crystalline form of Nilotinib Butanedisulfonate (2:1)

Crystalline Nilotinib butanedisulfonate (1 g) of Example 2 was suspended in methanol (20 ml) and was stirred at reflux for 60 min. The mixture was cooled to room temperature. Solid was filtered, washed with methanol (2 ml×3) and dried in air oven at 70-75° C. (yield: 0.8 g)

Example 6

Preparation of Nilotinib Butanedisulfonate (1:1) Crystalline Form IV

Nilotinib base (20 g) was suspended in methanol (800 ml) and 1,4-butanedisulfonic acid ~60% aqueous solution (6 ml) was added at 50-55° C., and was filtered to remove insoluble matter. Filtrate was stirred at room temperature for 2-3 h. Product formed was filtered, washed with methanol (20 ml×2) and dried the product in air oven at 70-75° C. (yield: 18.4 g).

Purity (by HPLC):99.86%

$^1$H NMR (400 MHz,DMSO-d6) δ 1.64-1.68(m,4H), 2.47-2.51(m,4H), 2.41(s,3H), 2.42(d,3H), 7.52(d,1H), 7.83-7.89 (m,2H), 7.99(s,1H), 8.15(s,1H), 8.36 (d,1H), 8.39(s,1H), 8.65-8.66(m,2H), 8.79(d,1H), 8.89(br s,1H), 9.36(s,1H), 9.41(br s,1H), 9.74(d,1H), 10.91(s,1H).

Figure 4:
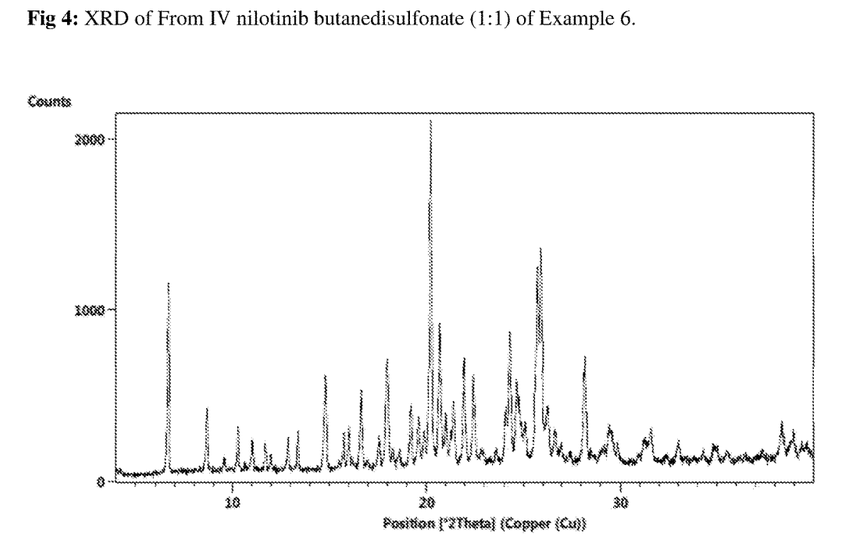
FIG. 4: XRD of From IV nilotinib butanedisulfonate (1:1) of Example 6.

The salt has XRPD pattern substantially same as set forth in FIG. 4.

Example 7

Preparation of Nilotinib 1,5-napthalenedisulfonic acid Salt (2:1) Crystalline Form V Nilotinib base (1 g) was suspended in water (20 ml). A solution of 1,5-napthalenedisulfonic acid (0.4 g; 0.6 eq.) in water (5 ml) was added and the content was heated at 50-55° C. for 1 h. The mixture was cooled to 25-30° C., filtered and washed with water (10 ml). The product was dried in air oven at 50-55° C. (yield: 1.2 g).

$^1$H NMR (400 MHz,DMSO-d6) δ 2.39 (s,3H), 2.42 (s,3H), 7.45-7.61 (m,4H),7.84 (d,1H), 7.97(s,2H),8.08 (m,1H),8.31 (s,1H) 8.38 (s,1H),8.55 (d,1H), 8.63 (s,2H), 8.75 (s,1H), 8.92 (d,1H), 9.26 (s, 1H), 9.34 (s,1H),9.62 (s,1H), 10.85 (s,1H).

Figure 5:
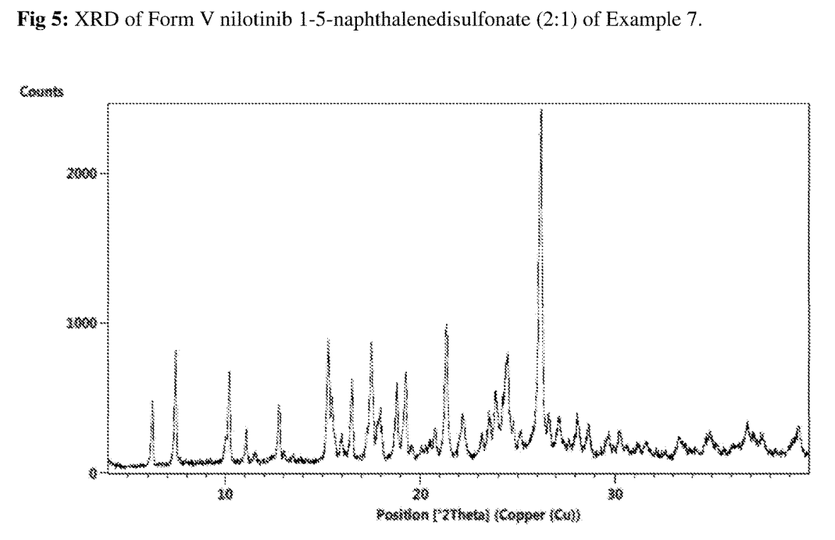
FIG. 5: XRD of Form V nilotinib 1-5-naphthalenedisulfonate (2:1) of Example 7.

The salt has a XRPD pattern substantially same as set forth in FIG. 5.

Example 8

Preparation of Nilotinib 1,5-napthalenedisulfonic acid Salt (1:1) Crystalline Form VI Nilotinib base (1 g) was suspended in water (20 ml). A solution of 1,5-napthalenedisulfonic acid (0.8 g; 1.2 eq) in water (5 ml) was added and the content was heated at 50-55° C. for 1 h. The mixture was cooled to 25-30° C., filtered, washed with water (10 ml) and dried in air oven at 50-55° C. (yield: 1.4g).

$^1$H NMR(400 MHz,DMSO-d6) δ 2.40 (s,3H),2.41 (s,3H), 7.43-7.52 (m,3H),7.61 (d,1H), 7.85-7.99(m,5H),8.11 (s,1H), 8.34 (s,2H), 8.64-8.67 (m,2H), 8.89-8.92 (m,4H),9.40(d, 2H), 9.72 (s,1H), 10.87 (s,1H).

Figure 6:
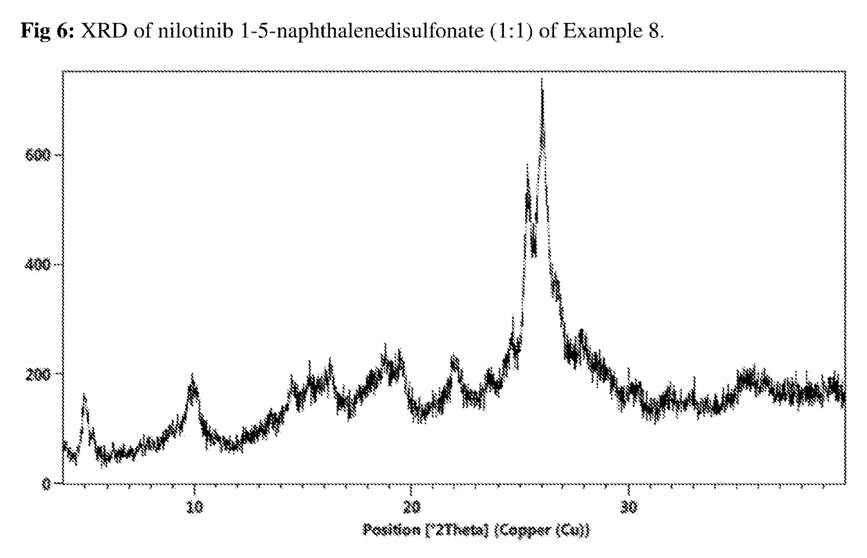
FIG. 6: XRD of Form VI nilotinib 1-5-naphthalenedisulfonate (1:1) of Example 8.

The salt has a XRPD pattern substantially same as set forth in FIG. 6.

Example 9

Preparation of Nilotinib napthalene-1-sulfonic acid Salt Crystalline Form VII

Nilotinib base (1 g) was suspended in water (10 ml) and heated to 50-55° C. A solution of napthelene-1-sulfonic acid and methanol (10 ml) was added to it and heated at 70-75° C. for 30 min. The mixture was cooled to 25-30° C. and stirred for 10 min. The product was filtered, washed with water (2×2 ml) and dried under vacuum for 1-2 h at 50-55° C. $^1$H NMR (400 MHz,DMSO-d6) δ 2.41 (s,3H),2.42 (s,3H), 7.46-7.58 (m,5H), 7.70-8.00 (m,7H)8.11(s,1H)8.31 (s,1H),8.37(s,1H),8.63-8.66 (m,3H), 8.81-8.89 (m,2H), 9.31 (s,1H), 9.37 (d,1H), 9.71 (d,1H), 10.86 (s,1H)

Figure 7:
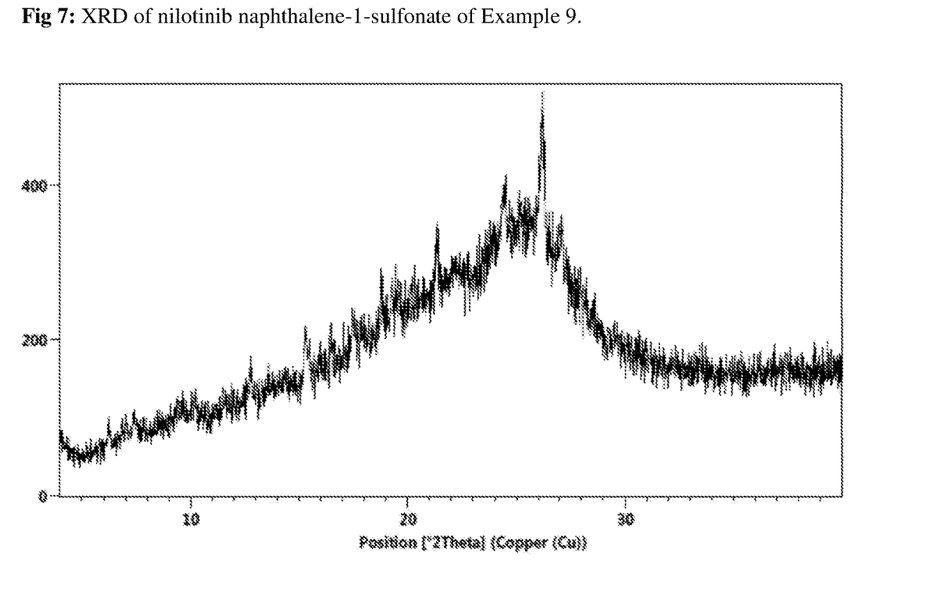
FIG. 7: XRD of Form VII nilotinib naphthalene-1-sulfonate of Example 9.

The salt has a XRPD pattern substantially same as set forth in FIG. 7.

Example 10

Preparation of Nilotinib 1-hydroxy-2-napthoic acid Salt Crystalline Form VIII

Nilotinib base (1 g) was suspended in water (20 ml) and heated to 50-55° C. 1-Hydroxy-2-napthoic acid was added to it and the content was heated at 50-55° C. for 1 h. Methanol (5 ml) was added to the mixture and stirred for 30 min. The content was filtered, washed with water (2×2 ml) and dried under vacuum for 1 h at 50-55° C. $^1$H NMR (400 MHz, DMSO-d6) δ 2.25 (s,3H), 2.41 (s,3H), 7.40-7.92 (m,11H), 8.23-8.73 (m,8H), 9.24 (s,1H), 9.34(s,1H), 10.70 (s,1H).

Figure 8:
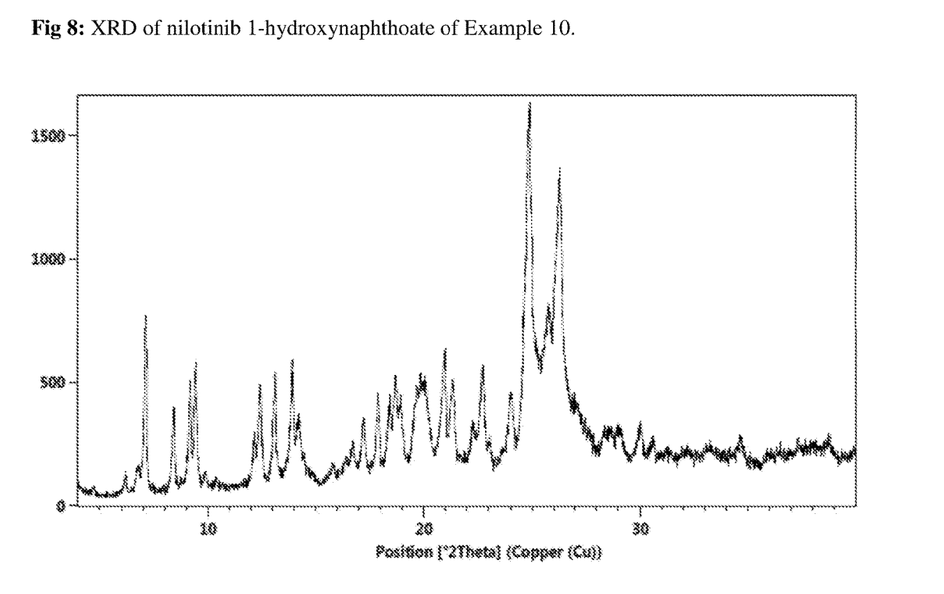
FIG. 8: XRD of Form VIII nilotinib 1-hydroxynaphthoate of Example 10.

The salt has a XRPD pattern substantially same as set forth in FIG. 8.

The invention claimed is:

1. An acid addition salt of nilotinib wherein the acid is 1,4-butanedisulfonic acid.

2. A crystalline Form 1 of nilotinib benzenesulfonate having an X-ray powder diffraction pattern comprising characteristic peaks at 7.2, 14.5, 18.8 and 24.2±0.2 degrees 2θ.

3. The crystalline Form 1 as in claim 2 having an X-ray powder diffraction pattern comprising further characteristic peaks at 20.7, 25.7, 26.2 and 29.1±0.2 degrees 2θ.

4. The acid addition salt of nilotinib as in claim 1, wherein the mole ratio of nilotinib to 1,4-butanedisulfonic acid is 2:1.

5. A crystalline Form II of 2:1 salt of nilotinib with 1,4-butanedisulfonic acid having water content of 3% to 9%.

6. The crystalline Form II as in claim 5 having an X-ray powder diffraction pattern comprising characteristic peaks at 5.9, 8.1, 26.3 and 26.9±0.2 degrees 2θ.

7. The crystalline Form II as in claim 6 having an X-ray powder diffraction pattern comprising further characteristic peaks at 19.6, 21.1, 21.9 and 27.5±0.2 degrees 2θ.

8. A crystalline Form III of 2:1 salt of nilotinib with 1,4-butanedisulfonic acid having water content of less than 1%.

9. The crystalline Form III as in claim 8 having an X-ray powder diffraction pattern comprising characteristic peaks at 10.0, 20.3, 20.9 and 25.2±0.2 degrees 2θ.

10. The crystalline Form III as in claim 9 having an X-ray powder diffraction pattern comprising further characteristic peaks at 5.8, 14.9, 17.3 and 25.9±0.2 degrees 2θ.

11. The acid addition salt of nilotinib as in claim 1, wherein the mole ratio of nilotinib to 1,4-butanedisulfonic acid is 1:1.

12. A crystalline Form IV of 1:1 salt of nilotinib with 1,4-butanedisulfonic acid having an X-ray powder diffraction pattern comprising characteristic peaks at 6.7, 20.2, 20.7, 24.3, and 25.7±0.2 degrees 2θ.

13. The crystalline Form IV as in claim 12 having an X-ray powder diffraction pattern comprising further characteristic peaks at 14.8, 16.6, 17.9 and 28.2±0.2 degrees 2θ.

14. A crystalline Form V of 2:1 salt of nilotinib with 1,5-naphthalene sulfonic acid having an X-ray powder diffraction pattern comprising characteristic peaks at 15.3, 17.5, 21.3 and 26.2±0.2 degrees 2θ.

15. The crystalline Form V as in claim 14 having an X-ray powder diffraction pattern comprising further characteristic peaks at 7.5, 10.2, 18.8 and 19.3±0.2 degrees 2θ.

16. A crystalline Form VI of 1:1 salt of nilotinib with 1,5-naphthalene sulfonic acid having an X-ray powder diffraction pattern comprising characteristic peaks at 18.8, 19.5, 25.4 and 26.1±0.2 degrees 2θ.

17. The crystalline Form VI as in claim 16 having an X-ray powder diffraction pattern comprising further characteristic peaks at 5.0, 9.9, 16.3 and 24.6±0.2 degrees 2θ.

18. A crystalline Form VII of nilotinib naphthalene-1-sulfonate having an X-ray powder diffraction pattern comprising characteristic peaks at 21.4, 24.5, 26.2 and 27.1±0.2 degrees 2θ.

19. The crystalline Form VII as in claim 18 having an X-ray powder diffraction pattern comprising further characteristic peaks at 12.8 and 15.3±0.2 degrees 2θ.

20. A crystalline Form VIII of a salt of nilotinib with 1-hydroxynaphthoic acid having an X-ray powder diffraction pattern comprising characteristic peaks at 7.2, 24.9, 25.8 and 26.3±0.2 degrees 2θ.

21. The crystalline Form VII as in claim 20 having an X-ray powder diffraction pattern comprising further characteristic peaks at 9.2, 9.5, 13.1 and 13.9±0.2 degrees 2θ.

22. A medicine comprising the acid addition, or crystalline form of, salt of nilotinib as claimed in claim 1.

23. A method of treating Philadelphia chromosome positive chronic myeloid leukemia in a subject in need thereof comprising administering to the subject a therapeutically effective amount of an acid addition, or crystalline form of, salt of nilotinib as claimed in any one of claims 1, 5, 8 or 12.

24. The method as claimed in claim 23 wherein the disease is leukemia.

25. The method of claim 24, wherein the leukemia is chronic myeloid leukemia.

* * * * *